United States Patent [19]

Griswold et al.

[11] Patent Number: 5,006,835
[45] Date of Patent: Apr. 9, 1991

[54] REMOTE CALIBRATING FOR PRESSURE TRANSDUCER

[75] Inventors: Allen B. Griswold, North Falmouth; Paul A. Tessier, Hudson; Drew G. Koschek, Ashland, all of Mass.

[73] Assignee: Hewlett-Packard Company, Palo Alto, Calif.

[21] Appl. No.: 568,653

[22] Filed: Aug. 14, 1990

Related U.S. Application Data

[63] Continuation of Ser. No. 83,749, Aug. 7, 1987, abandoned.

[51] Int. Cl.$^5$ .............................................. G08B 21/00
[52] U.S. Cl. ...................................... 340/626; 73/753; 73/4 R; 128/675
[58] Field of Search ................. 340/626; 73/4 R, 4 D, 73/4 V, 700, 753, 756; 128/672–675, 748; 364/571, 571.01

[56] References Cited

U.S. PATENT DOCUMENTS

| | | | |
|---|---|---|---|
| 3,748,656 | 7/1973 | Gray et al. | 340/626 |
| 4,494,106 | 1/1985 | Smith et al. | 340/626 |
| 4,603,574 | 8/1986 | Norman | 73/4 R |
| 4,658,829 | 4/1987 | Wallace | 128/675 |
| 4,672,974 | 6/1987 | Lee | 73/4 R |
| 4,736,155 | 4/1988 | McBrien | 73/725 |
| 4,760,730 | 8/1988 | Frank | 73/4 R |
| 4,800,749 | 1/1989 | Merrick | 73/4 R |
| 4,817,022 | 3/1989 | Jornod et al. | 73/4 R |

FOREIGN PATENT DOCUMENTS 3244738 6/1984 Fed. Rep. of Germany ...... 340/626

Primary Examiner—Joseph A. Orsino
Assistant Examiner—Jill Jackson
Attorney, Agent, or Firm—Richard F. Schuette

[57] ABSTRACT

A pressure transducer having a first pair leads for receiving an excitation voltage and a second pair of leads between which it can supply a voltage corresponding to a pressure applied to it is provided with means for placing at least one electrical load between said first pair of leads. The leads are connected to a pressure monitor having means for indicating the pressure represented by the voltage between said second pair of leads and means for indicating an alarm condition when said signal indicates a pressure outside of a given limit. The monitor has local means for disabling the alarm indicating means and means for setting the indicated pressure to zero. The monitor also has means responsive to a first given current in said first pair of leads for disabling said means for indicating an alarm and means responsive to a second given current in said first pair of leads for causing said means for indicating pressure to indicate a zero pressure.

6 Claims, 2 Drawing Sheets

REMOTE CALIBRATING FOR PRESSURE TRANSDUCER

CROSS REFERENCE TO RELATED APPLICATION

This application is a continuation of application Ser. No. 07/083,749, filed Aug. 7, 1987, now abandoned.

BACKGROUND OF THE INVENTION

FIG. 1 illustrates the equipment usually used in monitoring the blood pressure of a patient at some point in his blood circulation system. One end of a catheter C is inserted through the blood vessels to that point, and the other end is connected to a port on a t connector 2. A bottle 3 of saline solution is coupled via a tube 4, a valve V1 and a fast/slow flush device f to another port of the t connector 2, and a third port of the t connector 2 is coupled via a tube 5 and a valve $V_2$ to a hollow cavity c in what is called a pressure dome D. A tube 6 that communicates with the cavity c is provided with a valve $V_3$, and the cavity c is covered by a pliable membrane m. A transducer T is provided that converts any pressure applied to its sensing surface S that is in contact with the membrane m into a corresponding electrical signal. An exciting voltage that is required by the type of transducer used is supplied by a monitor M via leads $L_1$ and $L_2$, and the output pressure signal from the transducer T is coupled to the monitor M by leads $L_3$ and $L_4$ so as to control a pressure indicator I. The monitor M and the transducer T may be at some distance from each other.

After the catheter C, the tubes 5 and 6 and the cavity c have been filled with saline solution, a zero setting of the monitor pressure indicator is attained by the following steps. This procedure will be described by assuming that, as quite often occurs, the monitor M and the transducer T are on opposite sides of the patient's bed.

1. In order to prevent any alarms from being asserted during the zero calibration, a control A on the monitor M is activated so as to disable the alarm.

2. After walking around the bed, the nurse closes $V_2$ and opens $V_3$ so that atmospheric pressure is applied to the surface S of the transducer T.

3. In order to adjust the zero setting of the monitor, it is necessary to walk around the bed a second time so as to activate the zero setting control Z on the monitor M.

4. A third trip around the bed is required to close $V_2$ and open $V_3$ so that the blood pressure will be applied to the transducer T.

5. A fourth trip around the bed is required to activate the alarms with the control A.

BRIEF SUMMARY OF THE INVENTION

By using this invention, the zero calibration of a monitor and transducer can be carried out at the monitor or at any point along the leads conveying the excitation voltage to the transducer by connecting means to said leads for selectively changing the current flowing through them. One way to accomplish this is to connect two series circuits, respectively, comprised of a normally open switch, $S_1$ and an electrical impedance $R_1$ and a normally open switch $S_2$ and a resistor $R_2$ between the leads $L_1$ and $L_2$ that convey the excitation voltage from terminals $t_1$ and $t_2$ of the monitor M to the transducer T. The impedances may have different values so that different current flows in the excitation circuit when each switch is closed by itself. Means, not shown, are provided in the monitor M for responding to the current resulting from the closure of one switch to turn off the alarms and for responding to the current resulting from the closure of the other switch to establish the zero setting. Instead of operating one switch at a time different currents could be caused to flow in the excitation circuit by closing one switch and then both, in which event the impedances could be the same or different. Alternatively, one switch could be used that temporarily disables the alarm and establishes a zero reference when activated and which reenables the alarm when deactivated. The invention can be used regardless of the kind of excitation voltage supplied by the monitor. Signals from the transducer T that represent pressure are implied via leads $L_3$ and $L_4$ to the terminals $t_3$ and $t_4$ of the monitor M.

In order to prevent accidental momentary closure of a switch from having any effect, the monitor is preferably provided with means for preventing the actuation of the alarm disabling circuit or the zero setting circuit unless a switch is closed for a given length of time such as two seconds.

If the monitor has no alarms, or if the disabling of alarms arms not required, only one switch and impedance is needed.

DETAILED DESCRIPTION OF THE INVENTION

Figure 2:
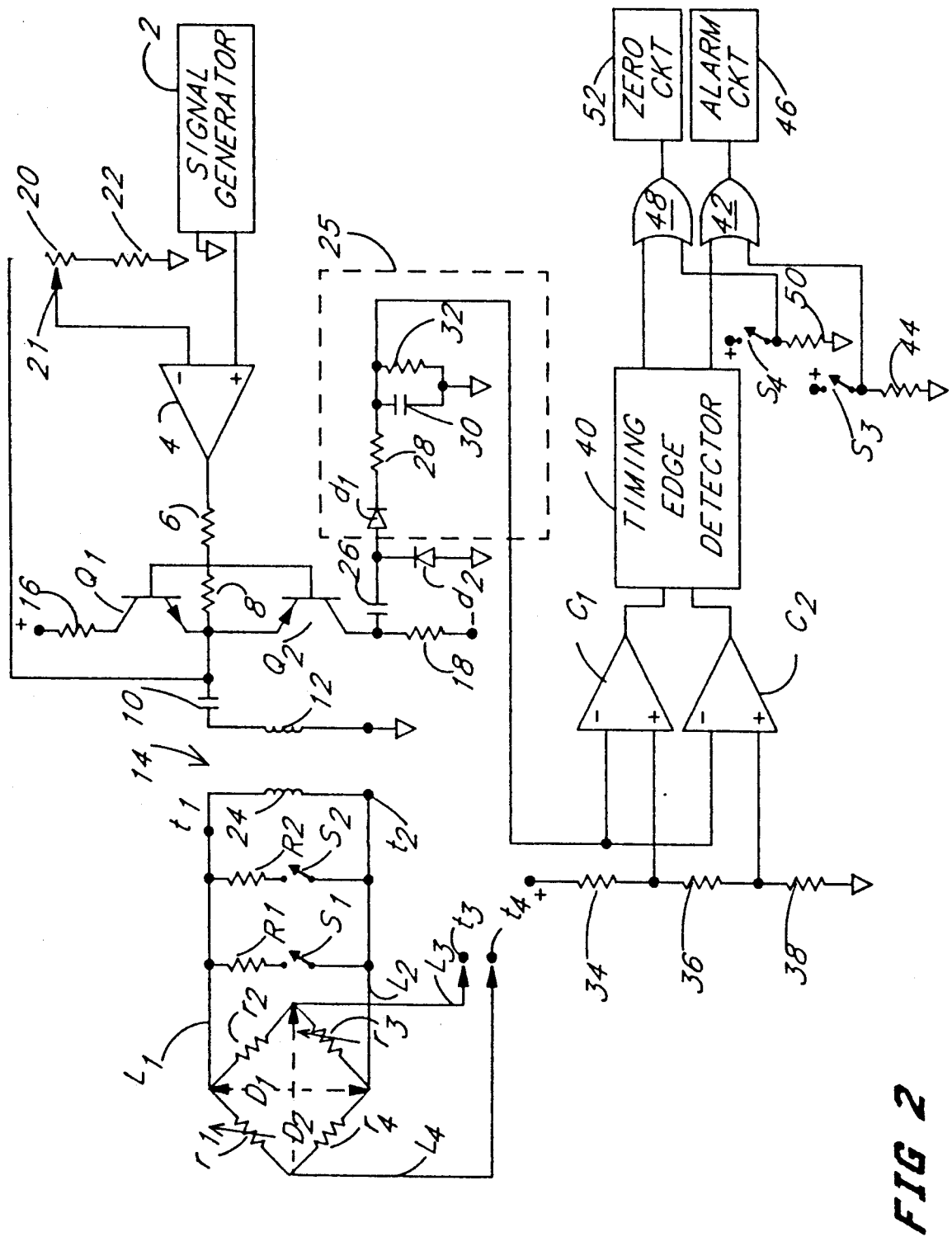
FIG. 2 is a schematic of one circuit that may be used to carry out the invention.

In FIG. 2 the ungrounded output of a signal generator 2 of sinusoidal voltage that is contained in the monitor M is connected to the + input of an operational amplifier 4, and its output is connected via resistors 6, 8 and a capacitor 10 to one end of the primary winding 12 of a transformer 14. The other end of the winding 12 is connected to ground. The base electrodes of transistors $Q_1$ and $Q_2$ are connected to the junction of the resistors 6 and 8, and their emitters are connected to the junction of the resistor 8 and the capacitor 10. A positive voltage point is connected to the collector of $Q_1$ via a resistor 16, and a negative voltage point is connected to the collector of $Q_2$ via a resistor 18. Feedback for the amplifier 4 is provided by connecting a potentiometer 20 and a resistor 22 in series between the junction of the resistor 8 and capacitor 10 and ground. A moveable tap 21 of the potentiometer 20 is connected to the − input of the amplifier 4, thereby providing means for varying its gain. The purpose of the resistor 8 is to provide current when neither $Q_1$ or $Q_2$ is conducting. A secondary winding 24 of the transformer 14 is connected between monitor terminals $t_1$ and $t_2$ of the monitor M.

In this illustrated embodiment, the transducer T is shown as having a bridge B comprised of resistors $r_1$, $r_2$, $r_3$, and $r_4$ connected in series, but it will be understood that other impedance elements such as capacitors or inductors could be used. The leads $L_1$ and $L_2$ are respectively connected to opposite ends of a first diagonal $D_1$. The amount of voltage appearing across the other diagonal, $D_2$, can be made to vary with pressure by a transducer that varies the values of $r_1$ and $r_3$ in opposite senses. The voltage at one end of $D_2$ is conveyed to a signal input terminal $t_3$ of the monitor M via the lead $L_3$, and the voltage at the other end of the diagonal $D_2$ is conveyed via a lead $L_4$ to another signal input terminal $t_4$ of a monitor M.

During the normal operation, the bridge B draws a given maximum current through the resistors 16 and 18. In accordance with this invention, means are provided for selectively changing the amount of current flowing in $L_1$ and $L_2$. One way of doing this is to connect at least one series circuit comprised of an impedance and a switch between $L_1$ and $L_2$. In this illustration two such series circuits are used. One is comprised of a resistor $R_1$ and a switch $S_1$ and the other comprised of a resistor $R_2$ and a switch $S_2$. The switches $S_1$ and $S_2$ are biased to an open position. Closing $S_1$ places $R_1$ in shunt with the bridge B. $R_1$ is of such value as to cause the amplitude of the current that flows through the resistor 18 on one half cycle and through the resistor 16 on the other to exceed the maximum amplitude attained during normal operation. The circuit including $Q_1$ and $Q_2$ is one means for indicating the current in $L_1$ and $L_2$. Means are provided for indicating the maximum value of this current. In this case it is a rectifier 25 comprised of the following components. The collector of $Q_2$ is coupled to the anode of a diode $d_1$ and to the cathode of a diode $d_2$ via a DC decoupling capacitor 26. The anode of $d_2$ is connected to ground, and the cathode of $d_1$ is connected to ground via a series circuit comprised of a resistor 28 and a capacitor 30. A discharge resistor 32 is connected in shunt with the capacitor 30.

The output of the rectifier 25 is coupled to means for determining when its output voltage exceeds a first given value. The output of the rectifier 25 is connected to the + inputs of comparators $C_1$ and $C_2$. A voltage divider comprised of series resistors 34, 36, and 38 is connected between a point of positive voltage and ground. The junction of the resistors 34 and 36 is connected to the − input of $C_1$, and the junction of the resistors 36 and 38 is connected to the − input of $C_2$. The values of these resistors is such that the output of the rectifier 25 at the + input of $C_2$ exceeds the voltage applied to its − input when $S_1$ is closed and $S_2$ is open and exceeds the voltage applied to the − input of $C_1$ when $S_2$ is closed and $S_1$ is open. Thus when only $S_1$ is closed, $C_2$ changes state and applies a positive voltage to a circuit 40. The circuit 40 includes a delay circuit and an edge responsive circuit so as to provide a positive output to one input of an OR gate 42 only after $C_2$ has changed state for a given time such as two seconds. This prevents response to accidental momentary closure of the switch. The other input of the OR gate 42 is connected to ground via a resistor 44 so that the OR gate 42 changes state when $C_2$ changes state. The output of the OR gate 42 is applied to means 46 for disabling the alarm circuit of a monitor until the zero setting is made. Although this could be done by hard wired circuits, it is easier to do it with the monitor's microprocessor if it has one.

Figure 1:
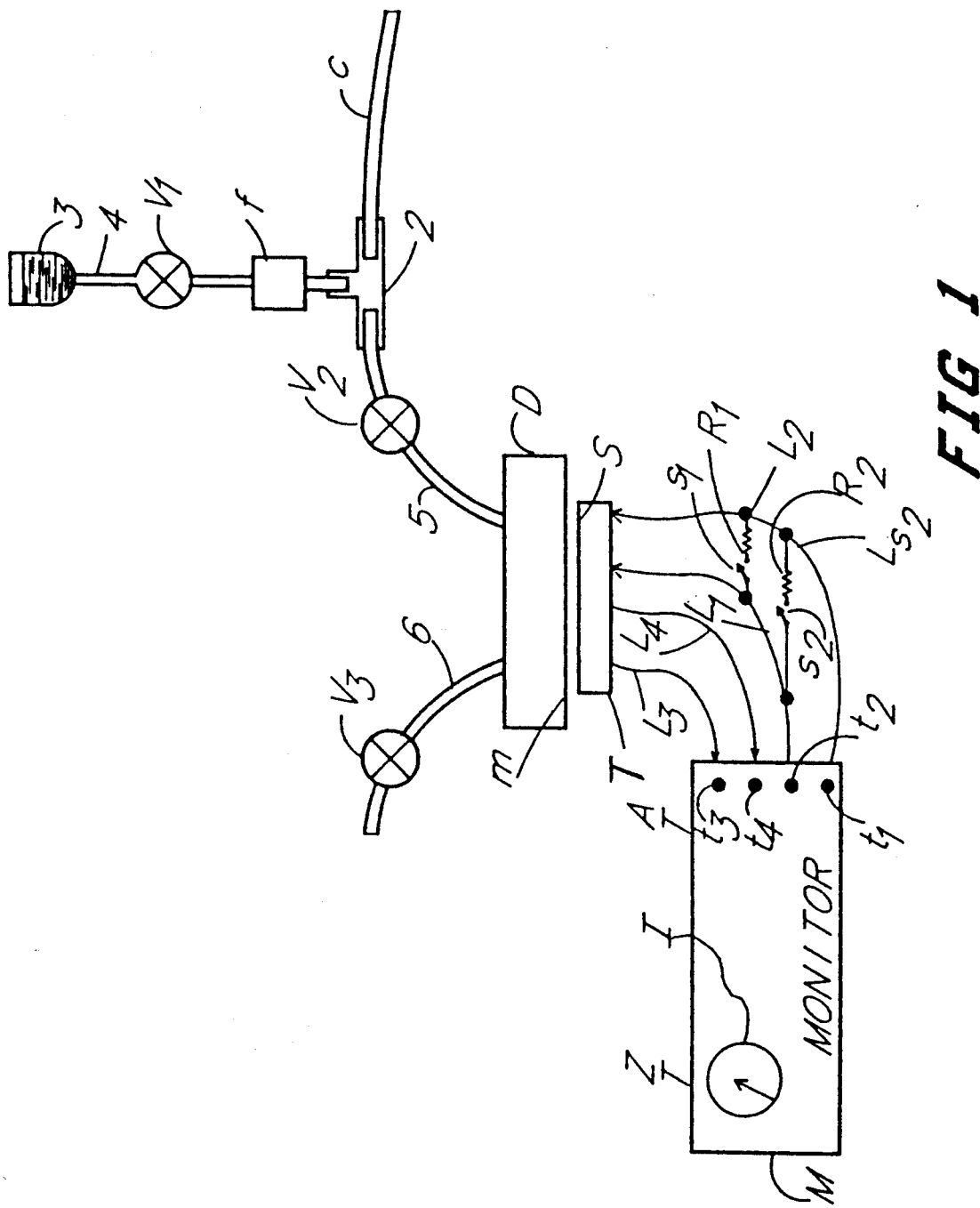
FIG. 1 is a block diagram representation of a blood pressure monitoring system.

$S_1$ may then be allowed to open and $S_2$ is closed so as to connect $R_2$ between $L_1$ and $L_2$. The value of $R_2$ is such as to cause more current to flow through the resistor 18 so that the rectified output appearing at the + inputs of $C_1$ and $C_2$ is sufficient to cause them to change state. The output of $C_1$ is also applied to the circuit 40, and a corresponding output thereof is connected to one input of an OR gate 48 after a suitable delay. A resistor 50 is connected between ground and the other input of the OR gate 48, and its output is connected to a circuit 52 in the monitor that sets its output at zero. This, of course, occurs when the sensitive surface S of the transducer is exposed to ambient pressure by the closing of $V_2$ and the opening of $V_3$ in FIG. 1.

The ability to adjust the zero setting of the monitor at the monitor when $S_1$ and $S_2$ are open is provided by connection of a switch $S_3$ between a point of positive voltage and the ungrounded end of the resistor 44 and by connecting a switch $S_4$ between a point of more positive voltage and the ungrounded end of the resistor 50. The closure of $S_3$ causes the OR gate 42 to change state and apply a voltage to the alarm disabling circuit 46. The closure of $S_4$ causes the OR gate 48 to change state and activate the zero setting circuit 52.

If for any reason it is desired to set the indicated pressure to zero without concern for an alarm condition, only one series switch and impedance would be required.

We claim:

1. A pressure monitor having
   a first pair of terminals,
   means for applying an excitation voltage for a transducer between said first pair of terminals,
   a second pair of terminals adapted for receiving a signal representing pressure from said transducer,
   means responsive to a signal between said second pair of terminals for indicating the pressure represented by the signal, and
   means within said monitor directly responsive to an arbitrary change in current through said first pair of terminals for calibrating said means for indicating pressure so that it indicates a pressure of zero when a zero pressure is applied to said transducer.

2. A pressure monitor as set forth in claim 1 further comprising:
   means responsive to a signal between said second pair of terminals for indicating an alarm condition when the pressure represented by the signal thereon passes a given limit, and
   means responsive to another arbitrary change in current in said first pair of terminals that is different from said first mentioned arbitrary change in current for disabling said means for indicating an alarm condition.

3. Apparatus comprising:
   a pressure transducer,
   a first pair of leads having first ends coupled to points in said transducer where excitation voltage is to be applied,
   a second pair of leads having first ends coupled to said transducer for conveying an output signal representing pressure that is supplied by said transducer,
   a monitor having means for applying an excitation voltage to second ends of said first pair of terminals and means coupled to second ends of said second pair of leads for indicating pressure in response to a signal on said second pair of leads,
   passive electrical impedance means,
   switching means for coupling said passive impedance means to at least one of said first pair of leads for selectively changing the current flowing in said first pair of leads by an arbitrary amount, and
   said monitor having means within it directly responsive to said arbitrary change in current flowing in said first pair of leads for calibrating said means for indicating pressure so that it indicates a pressure of zero when zero pressure is applied to said transducer.

4. Apparatus as set forth in claim 3 further comprising:
- means in said monitor for indicating an alarm condition in response to a signal on said second pair of leads being outside of a prescribed limit, and
- means in said monitor responsive to a different arbitrary change in current flowing in said first pair of leads caused by further operation of said switching means for disabling said means for indicating an alarm condition.

5. A pressure monitor having
- a first pair of terminals,
- means for applying an excitation voltage for a transducer between said first pair of terminals,
- a second pair of terminals for receiving a signal representing pressure from a transducer,
- means responsive to a signal between said second pair of terminals for indicating the pressure represented by the signal,
- means responsive to an arbitrary change in current through said first pair of terminals for calibrating said means for indicating pressure so that it indicates a pressure of zero when a zero pressure is applied to said transducer,
- means for responsive to a signal between said second pair of terminals for indicating an alarm condition when the pressure represented by the signal thereon passes a given limit, and
- means responsive to another arbitrary change in current in said first pair of terminals that is different from said first mentioned arbitrary change in current for disabling said means for indicating an alarm condition.

6. Apparatus comprising:
- a pressure transducer,
- a first pair of leads having first ends coupled to points in said transducer where excitation voltage is to be applied,
- a second pair of leads having first ends coupled to said transducer for conveying an output signal representing pressure that is supplied by said transducer,
- a monitor having means for applying an excitation voltage to second ends of said first pair of terminals and means coupled to second ends of said second pair of leads for indicating pressure in response to a signal on said second pair of leads,
- passive electrical impedance means,
- switching means for coupling said passive impedance means to at least one of said first pair of leads for selectively changing the current flowing in said first pair of leads by an arbitrary amount,
- said monitor having means responsive to said arbitrary change in current flowing in said first pair of leads for calibrating said means for indicating pressures so that it indicates a pressure of zero when zero pressure is applied to said transducer,
- means in said monitor for indicating an alarm condition in response to a signal on said second pair of leads being outside of a prescribed limit, and
- means in said monitor responsive to a different arbitrary change in current flowing in said first pair of leads caused by further operation of said switching means for disabling said means for indicating an alarm condition.

* * * * *